(12) United States Patent
Fries et al.

(10) Patent No.: US 11,585,815 B2
(45) Date of Patent: Feb. 21, 2023

(54) METHOD FOR DIAGNOSIS OF A BENIGN RENAL ONCOCYTOMA BY MEANS OF VIM3

(71) Applicant: Universität Zu Köln, Cologne (DE)

(72) Inventors: Jochen Fries, Pulheim (DE); Melanie Von Brandenstein, Lindlar (DE)

(73) Assignee: UNIVERSITÄT ZU KOLN, Cologne (DE)

( * ) Notice: Subject to any disclaimer, the term of this patent is extended or adjusted under 35 U.S.C. 154(b) by 53 days.

(21) Appl. No.: 14/779,536

(22) PCT Filed: Mar. 25, 2014

(86) PCT No.: PCT/EP2014/055955
§ 371 (c)(1),
(2) Date: Sep. 23, 2015

(87) PCT Pub. No.: WO2014/154686
PCT Pub. Date: Oct. 2, 2014

(65) Prior Publication Data
US 2016/0047814 A1   Feb. 18, 2016

(51) Int. Cl.
*C12Q 1/6886* (2018.01)
*G01N 33/574* (2006.01)

(52) U.S. Cl.
CPC ..... *G01N 33/57438* (2013.01); *C12Q 1/6886* (2013.01); *C12Q 2600/112* (2013.01); *C12Q 2600/158* (2013.01)

(58) Field of Classification Search
CPC .............................................. G01N 33/57438
USPC ....................................................... 435/7.23
See application file for complete search history.

(56) References Cited

U.S. PATENT DOCUMENTS

| | | | | |
|---|---|---|---|---|
| 7,354,584 B2 * | 4/2008 | Reed | ...................... | C07K 16/244 424/133.1 |
| 2004/0121419 A1 * | 6/2004 | Markovitz | .............. | C07K 16/18 435/7.92 |
| 2004/0175744 A1 * | 9/2004 | Hu | ........................ | C12Q 1/6886 435/6.14 |
| 2004/0213791 A1 * | 10/2004 | Bander | ............... | A61K 51/1072 424/155.1 |
| 2005/0130193 A1 * | 6/2005 | Luxon | .................. | C12Q 1/6886 435/6.14 |
| 2007/0059806 A1 * | 3/2007 | Arnon | ................... | C12N 15/115 435/91.1 |
| 2011/0052642 A1 * | 3/2011 | Scheffler | .............. | C12N 5/0693 424/277.1 |

FOREIGN PATENT DOCUMENTS

| WO | 2005/024603 A2 | 3/2005 |
|---|---|---|
| WO | WO-2005/024603 A2 | 3/2005 |
| WO | 2011/137519 A1 | 11/2011 |
| WO | WO-2011/137519 A1 | 11/2011 |

OTHER PUBLICATIONS

Paul, Fundamental Immunology, 3rd Edition, 1993, pp. 292-295 (Year: 1993).*
Rudikoff et al. (Proceedings of the National Academy of Sciences USA, vol. 79, p. 1979-1983, 1982) (Year: 1982).*
Mickisch et al (World J Urol, 2005, 23: 191-195).*
Von Brandenstein et al., Vimentin 3, the new hope, differentiating RCC versus oncocytoma. Disease Markers. 2015;2015:368534, pp. 1-8.
Anonymous Vimentin variant 3 [*Homo sapiens*] PubMed.gov Feb. 20, 2008. <www.ncbi.nlm.nih.gov/protein/ACA06103.1> Retrieved on Sep. 22, 2015.
Anonymous "Vimentin variant 3", Unitpro.org Apr. 8, 2008. <www.uniprot.org/uniprot/BOYJC4 > retrieved on Sep. 22, 2015.
Von Brandenstein Melanie et al. "MicroRNA 15a, Inversely Correlated to PKC alpha, Is a Potential Marker to Differentiate between Benign and Malignant Renal Tumors in Biopsy and Urine Samples." American Journal of Pathology. 180(5):1787-1797 (2012).
Ondrej Hes et al. "Vimentin reactivity in renal oncocytoma—Immunohistochemical study of 234 cases." Archives of Pathology & Laboratory Medicine. 131(12):1782-1788 (2007).
Thakkar Dipti et al. "Proteomic Studies Coupled with RNAi Methodologies can Shed Further Light on the Downstream Effects of Telomerase in Glioma", Cancer Investigation, 29(2): 113-122 (2011).
Geramizadeh Bita et al. "Useful markers for differential diagnosis of oncocytoma, chromophobe renal cell carcinoma and conventional renal cell carcinoma." Indian Journal of Pathology & Microbiology. 51(2):167-171 (2008).
Jochen Fries et al. "Vim3 Antibody—Use of Vimentin 3 for diagnosis and of Vimentin 3 for diagnosis and differentiation of benign and malignant renal carcinoma." Eapb.org Feb. 4, 2014. <www.eapb.org/fileadmin/Attachement/events14/PosterProvendis_3.pdf>.
Jochen Fries et al. "Vim 3 antibody—Use of Vimentin 3 for the diagnosis and differentiation of benign and malignant renal carcinoma." Biovara.org May 9, 2014. <www.biovaria.org/uploads/txbiotechnologies/P1Vim3friesvbrandensteTn14Q422.pdf>.
Bohn et al. (Jul. 1992) "Species-specific recognition patterns of monoclonal antibodies directed against vimentin," Exp Cell Res. 201(1):1-7.
Esue et al. (2006) "A direct interaction between actin and vimentin filaments mediated by the tail domain of Vimentin," J Biol Chem. 281:30393-30399.
Fontenete et al. (2011) "Controversies in using urine samples for Prostate Cancer detection: PSA and PCA3 expression analysis," Clinical Urology. 37(6):719-726.

(Continued)

*Primary Examiner* — Sean E Aeder
(74) *Attorney, Agent, or Firm* — Raphael Bellum PLLC

(57) ABSTRACT

The present invention relates to a method for the diagnosis of a benign oncocytoma and a method to differentiate a benign oncocytoma from malignant renal cell carcinoma, a kit for use in these methods, as well as antibody relating thereto, a hybridoma cell capable of producing the same as well as the uses relating thereto.

Figure 1:
Figure 1:
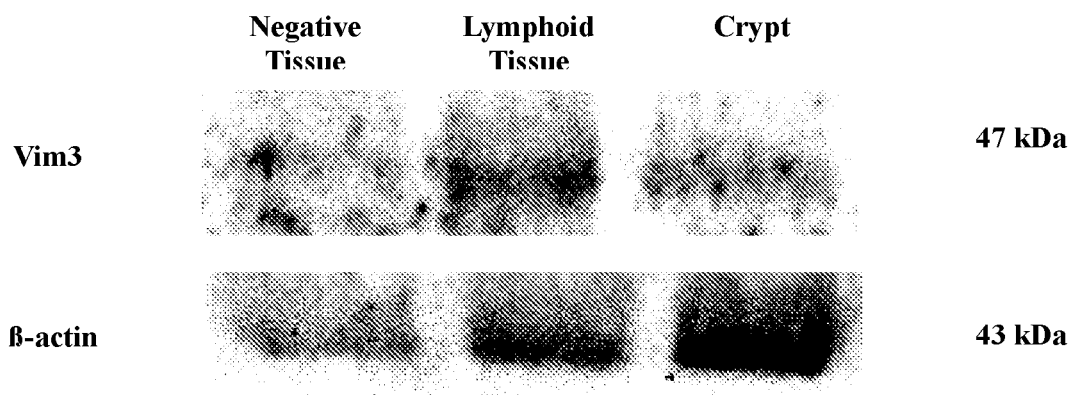

3 Claims, 6 Drawing Sheets
Specification includes a Sequence Listing.

(56) References Cited

OTHER PUBLICATIONS

Georgatos et al. (1987) "Lamin B constitutes an intermediate filament attachment site at the nuclear envelope," J Cell Biol. 105:117-125.
Gerstung et al. (2007) "Endothelin-1 induces NF-kappaB via two independent pathways in human renal tubular epithelial cells," Am J Nephrol. 27:294-300.
Hanke et al. (2007) "Detailed Technical Analysis of Urine RNA-Based Tumor Diagnostics Reveals ETs2/Urokinase Plasminogen Activator to Be a Novel Marker for Bladder Cancer," Clinical Chemistry. 53(12):2070-2077.
Ivaska et al. (2007) "Novel fimctions of vimentin in cell adhesion, migration, and signaling," Exp Cell Res. 313:2050-2062.
Kataoka et al. (1991) "Ultrastructural study of mitochondria in oncocytes," Ultrastruct Pathol. 15:231-239.
Klein et al. (1976) "Proximal tubulär adenomas of kidney with so-called oncocytic features: A clinicopathologic study of 13 cases of a rare ly reported neoplasm," Cancer. 38:906-914.
Krüger et al. (2005) "Expression of KIT (CD117) in Renal Cell Carcinoma and Renal Oncocytoma," Oncology. 68:269-275.
Lin et al. (2004) "Immunohistochemical Detection of P504S in Primary and Metastatic Renal Cell Carcinomas," Appl Immunohistochem Mol Morphol. 12:153-159.
Malakoutikhah et al. (2011) "The use of chimeric vimentin citrullinated peptides for the diagnosis of rheumatoid arthritis," J Med Chem. 54:7486-7492.
Matignon et al. (2014) "Urinary Cell mRNA Profiles and Differential Diagnosis of Acute Kidney Graft Dysfunction," J Am Soc Nephrol. 25:1586-1597.
Molinié et al. (2006) "Alpha-methyl CoA racemase expression in renal cell carcinomas," Human Pathology. 37:698-703.
Ondrej et al. (Dec. 13, 2007) "Vimentin reactivity in renal oncocytoma—Immunohistochemical study of 234 cases," Archives of a Pathology & Laboratory Medicine. 131(12):1782-1788.
Osunkoya et al. (2009) "Claudin-7 and claudin-8: immunohistochemical markers for the differential diagnosis of chromophobe renal cell carcinoma and renal oncocytoma," Hum Pathol. 40:206-210.
Oxley et al. (2007) "Metastatic renal oncocytoma," J Clin Pathol. 60:720-722.
Pelosi et al. (2011) "Immunhistochemistry by Means of Widely Agreed-Upon Markers (Cytokeratins 5/6 and 7, p63, Thyroid Transcription Factor-1, and Vimentin) on Small Biopsies of Non-small Cell Lung Cancer Effectively Parallels the Corresponding Profiling and Eventual Diagnoses on Surgical Specimens," J. Thorac. Oncol. 6:1039-1049.
Sarria et al. (1994) "The presence or absence of a Vimentin-type intermediate filament network affects the shape of the nucleus in human SW-13 cells," J Cell Sci. 107(6):1593-1607.
Spurny et al. (2008) "Plectin deficiency affects precursor formation and dynamics of Vimentin networks," Exp Cell Res. 314:3570-3580.
Uma et al. (2007) "Identification of prostate cancer mRNA markers by averaged differential expression and their detection in biopsies, blood, and urine," PNAS. 104(7):2343-2348.
Von Brandenstein et al. (2008) "A p38-p65 transcription complex induced by endothelin-1 mediates signal transduction in cancer cells," Biochim Biophys Acta. 1783:1613-1622.
Von Brandenstein et al. (2011) "Protein kinase C alpha regulates nuclear pri-microRNA 15a release as part of endothelin signaling," Biochim Biophys Acta. 1813:1793-1802.
Waldherr et al. (1985) "Co-expression of cytokeratin and vimentin intermediate-sized filaments in renal cell carcinomas: Comparative study of the intermediate-sized filament distribution in renal cell carcinomas and normal human kidney," Virchows Arch A Pathol Anat Histopathol. 408:15-27.
Weikert et al. (2005) "Quantitative analysis of survivin mRNA expression in urine and tumor tissue of bladder cancer patients and its potential relevance for disease detection and prognosis," Int. J. Cancer. 116:100-104.
Hes et al., Vimentin reactivity in renal oncocytoma: immunohistochemical study of 234 cases, Arch Pathol Lab Med 2007, 131:1782-1788.
Thakkar et al., Proteomic studies coupled with RNAi methodologies can shed further light on the downstream effects of telomerase in glioma, Cancer Invest 2011, 29:113-122.
Von Brandenstein et al., MicroRNA 15a, inversely correlated to PKCalpha, is a potential marker to differentiate between benign and malignant renal tumors in biopsy and urine samples, Am J Pathol 2012, 180:1787-1797.
Vimentin variant 3 [*Homo sapiens*], ULR http://www.ncbi.nlm.nih.gov/protein/ACA06103.1, Feb. 20, 2008 (Feb. 20, 2008).
Vimentin variant 3, URL: http://www.uniprot.org/uniprot/B0YJC4, Apr. 8, 2008 (Apr. 8, 2008)A.
Von Brandenstein et al., MicroRNA 15a, Inversely Correlated to PKC alpha, Is a Potential Marker to Differentiate between Benign and Malignant Renal Tumors in Biopsy and Urine Samples, American Journal of Pathology; [10640], American Society for investigative Pathology, US, vol. 180, No. 5, May 1, 2012 (May 1, 2012), pp. 1787-1797.
Thakkar Dipti et al: "Proteomic Studies Coupled with RNAi Methodologies can Shed Further Light on the Downstream Effects of Telomerase in Glioma", Cancer Investigation, vol. 29, No. 2, Feb. 2011 (Feb. 2011), pp. 113-122.
Geramizadeh Bita et al: "Useful markers for differential diagnosis of oncocytoma, chromphobe renal cell carcinoma and conventional renal cell carcinoma.", Indian Journal of Pathology & Microbiology Apr.-Jun. 2008, vol. 51, No. 2, Apr. 2008 (Apr. 2008), pp. 167-171.
Jochen Fries et al., Vim3 antibody—Use of Vimentin3 for the diagnosis and differentiation of benign and malignant renal carcinoma, BioVaria Munich 2015, Jun. 17, 2014 (Jun. 17, 2014), URL:http://www.biovaria.org/programme/technologies/technologies-details/?tx_biotechn ologies_pi2%5buid%5d=121.
Use of Vimentin3 for the diagnosis and differentiation of benign and malignant renal carcinoma, URL: http://www.lifescienceslink.org/technologies-offered/use-of-vimentin3-for-the-diagnosis-and-differentiation-of-benign-and-malignant-renal-carcinoma/en, Feb. 25, 2014 (Feb. 25, 2014).
Jochen Fries et al., Vim3 Antibody—Use of Vimentin 3 for diagnosis and differentiation of benign and malignant renal carcinoma, Feb. 4, 2014 (Feb. 4, 2014), URL:http://www.eapb.org/fileadmin/Attachement/eventsI4/Poster_Provendis_3.pdf.
Jochen Fries et al., Vim 3 antibody—Use of Vimentin 3 for the diagnosis and differentiation of benign and malignant renal carcinoma, May 9, 2014 (May 9, 2014), URL:https://www.biovaria.org/uploads/tx_biotechnologies/PIVim3friesvbrandenstein 140422.pdf.
Genbank (Jun. 23, 2018) "Vimentin [Bos taurus]", Genbank Accession No. NP_776394.2, 7 pages.
Genbank (Jan. 29, 2018) "Vimentin [Cavia porcellus]", Genbank Accession No. NP_001166511.1, 1 page.
Genbank (Jun. 16, 2018) "Vimentin [Equus caballus]", Genbank Accession No. NP_001230074.1, 2 pages.
Genbank (Jan. 16, 2016) "Vimentin [Gallus gallus]", Genbank Accession No. NP_001041541.1, 3 pages.
Genbank (Apr. 18, 2005) "Vimentin [Mus musculus]", Genbank Accession No. CAA39807.1, 2 pages.
Genbank (Apr. 18, 2005) "Vimentin [Mus musculus]", Genbank Accession No. NP_035831.2, 1 page.
Genbank (Jun. 27, 2018) "Vimentin [Oncorhynchus mykiss]", Genbank Accession No. CAA90601.1, 2 pages.
Genbank (Jun. 23, 2018) "Vimentin [Pan troglodytes]", Genbank Accession No. NP_001009148.1, 7 pages.
Genbank (Jun. 23, 2018) "vimentin [Rattus norvegicus]", Genbank Accession No. NP_112402.1, 8 pages.
Genbank (Apr. 24, 2016) "Vimentin [Salmo salar]", Genbank Accession No. NP_001133947.1, 2 pages.
Genbank (Aug. 1, 2016) "Vimentin, Partial [Mesocricetus auratus]", Genbank Accession No. AAA37104.1, 1 page.
Hamperl (Dec. 1936) "Über das Vorkommen von Onkocyten in verschiedenen Organen und ihren Geschwüsten", Virchows Archiv für pathologische Anatomie und Physiologie und für klinische Medizin, 298(2):327-375. (English translation summary is submitted).

(56) References Cited

OTHER PUBLICATIONS

Zippel (Dec. 1941) "Zur Kenntnis der Onkocyten", Virchows Archiv für pathologische Anatomie und Physiologie und für klinische Medizin, 308(2):360-382. (English translation summary is submitted).

* cited by examiner

A

B

METHOD FOR DIAGNOSIS OF A BENIGN RENAL ONCOCYTOMA BY MEANS OF VIM3

INCORPORATION-BY-REFERENCE OF SEQUENCE LISTING

The contents of the text file named "P68415PCTSequencelisting.txt", which was created on Sep. 23, 2015, and is 5 KB in size, are hereby incorporated by reference in their entireties.

The present invention relates to a method for the diagnosis of a benign oncocytoma and a method to differentiate a benign oncocytoma from malignant renal cell carcinoma, a kit for use in these methods, as well as antibody relating thereto, a hybridoma cell capable of producing the same as well as the uses relating thereto.

Around 208,500 new cases of kidney cancer are diagnosed in the world each year, accounting for just under 2% of all cancers. The highest rates are recorded in Northern America and the lowest rates in Asian and African regions. Kidney tumors, also known as renal tumors, are tumors, or growths, on or in the kidney. These growths can be benign or malignant (cancerous). The most frequent, malignant, primary kidney cancer is renal cell carcinoma (RCC)—which has several subtypes including clear cell RCC, papillary RCC, chromophobe RCC and collecting duct RCC. However, kidney cancer can also be a metastatic tumour, e.g. ovarian carcinoma. Benign forms of kidney tumor include renal oncocytoma, cystic nephroma, angiomyolipoma, metanephric adenoma, renal medullary fibroma. A renal oncocytoma is a tumor of the kidney made up of oncocytes, a special kind of cell. Renal oncocytomas, first identified in 1942 (Zippel et al., 1942), have been regarded as predominantly benign renal neoplasms since the first study (Klein et al., 1976), although occasional reports of malignant cases have been reported (Oxley et al., 2007). The major diagnostic problem is the differential to other renal tumors: (i) the eosinophilic or granular form of clear cell carcinoma (cRCC) and (ii) the chromophobe renal carcinoma. Differential diagnosis currently uses immune histology to differentiate malignant renal cell carcinoma from oncocytoma. For chromophobe carcinoma, positivity for claudin 8 and negativity for claudin 7 have been shown as typical constellation (Osunkoya et al., 2009). To differentiate cRCC from oncocytoma, the positivity for Vimentin, a structural protein, has been used to identify the former (Waldherr et al., 1985).

An oncocyte is an epithelial cell characterized by an excessive amount of mitochondria. They were named in 1931 after the greek word "onkousthai" (to swell), and first described as a distinct cell system consisting of large epithelial cells with irregular nuclei and finely granular, acidophilic cytoplasm (Hamperl et al., 1936). The fundamental morphological nature of oncocytes, an abundance of mitochondria, was firmly established by electron microscopy (Kataoka et al., 1991). Since then, oncocytes have been detected in various organs (i.e. thyroid, parathyroid, salivary glands) as well as in different tumors (i.e. oncocytomas, Hürthle cell tumors of the thyroid, oxyphilic adenoma of parathyroid gland, Warthin's tumor of salivary gland) (Encyclopedia of Biol Chem 2004).

An oncocytoma is an epithelial tumor composed of oncocytes, large eosinophilic cells having small, round, benign-appearing nuclei with large nucleoli with excessive amounts of mitochondria. The treatment of benign oncocytoma differs from that of malignant renal carcinoma. For a malignant renal carcinoma, initial treatment is most commonly a radical or partial nephrectomy and remains the mainstay of curative treatment. Where the tumor is confined to the renal parenchyma, the 5-year survival rate is 60-70%, but this is lowered considerably where metastases have occurred. It is relatively resistant to radiation therapy and chemotherapy, although some cases respond to immunotherapy. Oncocytomas that are benign lesions and metastases are extremely uncommon. As they cannot be confidently pre-operatively distinguished from renal cell carcinomas in some cases, they are surgically resected. If the diagnosis is suspected pre-operatively then surgery by tumor enucleation can be performed. Accordingly, it is important to differentiate benign oncocytoma from malignant renal carcinoma.

Full length Vimentin positivity is currently used to differentiate between malignant renal carcinomas and benign oncytomas. Nowadays, it is common practice in pathology, to differentiate renal cell carcinomas from carcinomas of histogenetically different origins by immune histology with cytokeratins and Vimentin. Up to recently, Vimentin positivity has been considered as a significant advance not only for renal cell carcinoma in general but also to differentiate them from their benign counterparts, the oncocytomas. Recently a series of oncocytomas has been reported, in which a Vimentin positivity has been observed, making the differential questionable, particularly in preoperative evaluation (Hes et al., 2007). Hes et al. analysed 253 oncocytoma of which were 73% positive for Vimentin staining. Thus the accuracy and validity of this currently used diagnostic approach appears questionable. The question remains whether past "vimentin-positive oncocytomas" results are truly benign or malignant and whether this has resulted in misdiagnosis for the patient.

Accordingly, alternative methods for the differentiation of benign oncocytoma from malignant renal cell carcinoma and/or for the diagnosis of a benign oncocyctoma, which avoids the above disadvantages, are required. Particularly, the methods should be reliable, robust, accurate and easy to use. Furthermore, one of the aims of the present invention was to provide agents that are easily used and supplied in combination with common laboratory diagnostic equipment and test methods to produce quick and unbiased results.

Surprisingly, the inventors found that a splice isoform of Vimentin, namely Vimentin3 or Vim3, is an indicator of benign oncocytoma. Accordingly, Vim3 can be used in method for the differentiation of benign oncocytoma from malignant renal cell carcinoma and/or for negative) the diagnosis of a benign oncocyctoma.

Figure 5:
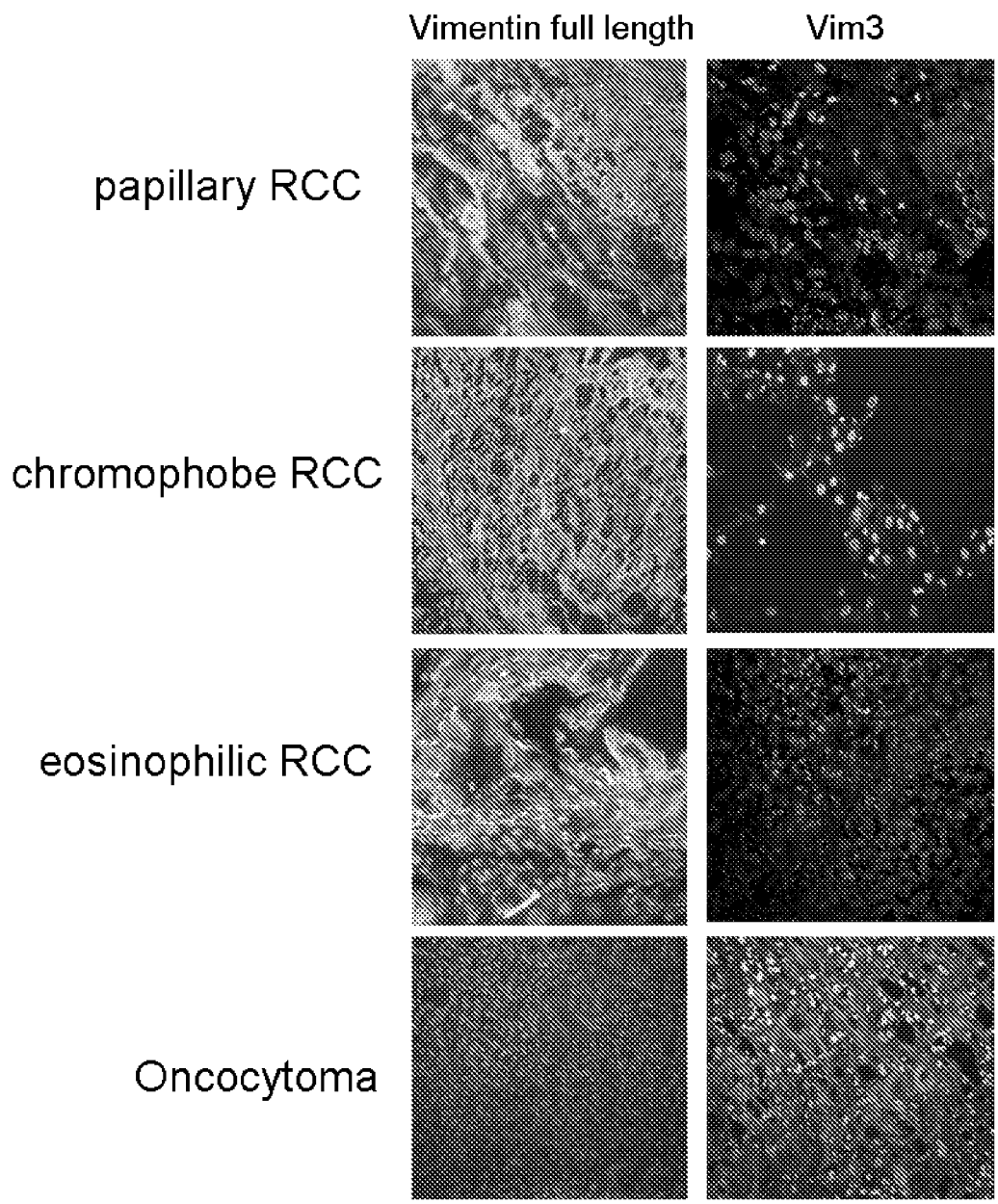
Figure 6:
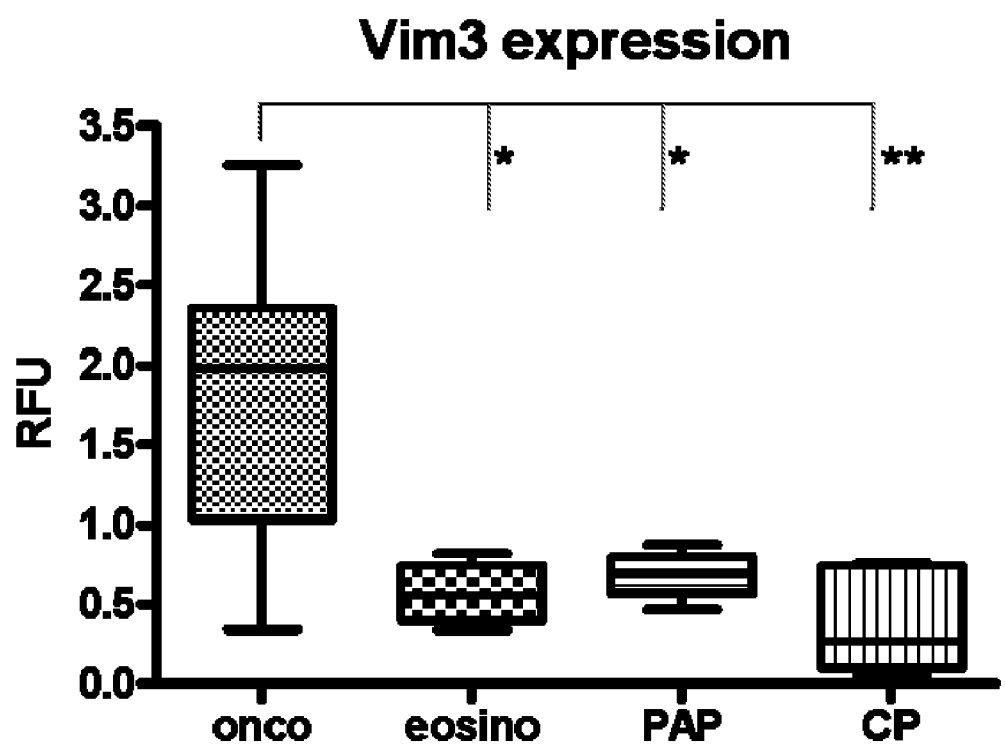

Particularly, the inventors found that renal cell carcinomas (RCCs) are negative for Vim3. However, Vim3 expression in RCCs may be induced by transforming growth factor beta (TGF-β) stimulation (see FIG. 2). In contrast thereto, benign oncocytomas were positive for Vim3 (see FIG. 3). Moreover, full length Vimentin was absent in benign oncocytomas, but high in RCCs. This finding (Vimentin being positive and Vim3 being negative) is true for clear cell RCCs, chromophobe RCC and papillary RCC (see FIG. 4). Therefore, the inventors have shown that Vim3 differentiates between benign and malignant kidney tumors (FIGS. 5 and 6).

Therefore in a first aspect, the present invention relates to a method for the diagnosis of a benign oncocytoma, comprising the step of detecting the presence or absence of Vim3 protein in a sample derived from a renal tumor, wherein the presence of Vim3 in the sample is indicative for a benign oncocytoma.

Furthermore, and in a related aspect, the present invention also relates to a method to differentiate a benign oncocytoma from malignant renal cell carcinoma, comprising the step of detecting the presence or absence of Vim3 protein in a sample derived from a renal tumor, wherein the presence of Vim3 protein in the sample is indicative for a benign oncocytoma.

Vim3 (also referred to as Vimentin3 or Vimentin variant 3) is a splice isoform of Vimentin. Vimentin itself is an intermediate sized filament that functions in signal transduction cellular function, structural integrity of cells and tissues and adhesion and migration (Ivaska et al., 2007). In 2007, a variant of Vimentin (Vim3) was described by a working group of the Craig Venter Institute (NHLBI Resequencing and Genotyping Service (RSG), N01-NV-48196, J. Craig Venter Institute, Rockville, Md. 20850). In 2011, the presence of this Vim3 in gliomas was described (Thakkar et al., 2011). However, no further analysis or investigation regarding its role has been performed.

Vim3 is a splice variant of Vimentin with a unique C-terminal ending. The human splice variant Vim3 is has 421 amino acids and is 35 amino acids smaller than the full length protein. Its unique structure leads to a 10 kDa smaller protein (FIG. 1B). The amino acid sequence of human Vim3 has been published and is available at UniProt KB Accession No. B0YJC4 (uniprot.org) or at the National Center for Biotechnology Information under GenBank Accession number ACA06103.1 (ncbinlm.nih.gov).

In the course of the present invention the inventors surprising found that an agent such as Vim3 protein could be easily and exclusively detected in oncocytoma e.g. by immune staining, making the detection of Vim3 a specific marker for this benign tumor. Vim3 protein was identified in different tissues (i.e. epithelium incl. proximal and distal renal tubules, lymphocytes, smooth muscle cells). By quantitative real time polymerase chain reaction (qRT-PCR), Vim3 transcripts were abundant in oncocytomas but low (absent) in malignant renal tumors (clear cell, papillary, chromophobe renal carcinoma). The reverse expression pattern was observed for full length Vimentin. In a preferred embodiment, Vim3 positive and full length Vimentin negative renal tumors are identified as benign oncocytomas.

An oncocytoma according to the present invention is an epithelial tumor composed of oncocytes, large eosinophilic cells having small, round, benign-appearing nuclei with large nucleoli with excessive amounts of mitochondria.

Renal cell carcinoma (RCC, also known as hypernephroma) according to present invention is a kidney cancer that may originate in the lining of the proximal convoluted tubule, the very small tubes in the kidney that transport GF (glomerular filtrate) from the glomerulus to the descending limb of the nephron. In the context of the present invention, the RCC is malignant.

A tumor (American English or tumour, British English) is commonly used as a synonym for a neoplasm (a solid or fluid-filled lesion that may or may not be formed by an

```
                              (SEQ ID NO: 1)
  1    mstrsvssss yrrmfggpgt asrpsssrsy vttstrtysl gsalrpstsr slyasspggv 61    yatrssavrl rssvpgvrll qdsvdfslad aintefkntr tnekvelqel ndrfanyidk 121    vrfleqqnki llaeleqlkg qgksrlgdly eeemrelrrq vdqltndkar veverdnlae 181    dimrlreklq eemlqreeae ntlqsfrqdv dnaslarldl erkveslqee iaflkklhee 241    eiqelqaqiq eqhvqidvdv skpdltaalr dvrqqyesva aknlqeaeew ykskfadlse 301    aanrnndalr qakqesteyr rqvqsltcev dalkgtnesl erqmremeen faveaanyqd 361    tigrlqdeiq nmkeemarhl reyqdllnvk maldieiaty rkllegeesr islplpnfss 421    lnlrgkhfis l
```

The Vimentin sequence of other species is also known, including e.g. *Mus musculus* (NCBI Accession: CAA39807.1, NP_035831.2), *Rattus norvegicus* (NCBI Accession: NP_112402.1), *Bos Taurus* (NCBI Accession: NP_776394.2), *Gallus gallus* (NCBI Accession: NP_001041541.1), *Mesocricetus auratus* (Accession: AAA37104.1), *Oncorhynchus mykiss* (Accession: CAA90601.1), *Equus caballus* (NP_001230074.1), *Salmo salar* (Accession: NP_001133947.1), *Pan troglodytes* (Accession: NP_001009148.1) and *Cavia porcellus* (Accession: NP_001166511.1). The splice variant corresponding to human Vim3 could be easily identified by sequence analysis and identification of homologues.

It is important to note that protein expression of Vimentin described in the literature by immune histology results from the combined detection not only of the protein from full length but also of the spliced variant of Vimentin, Vim3. In cases of eosinophilic appearing renal tumors, the differential diagnosis between RCCs and oncocytomas is based upon the presence or absence of Vimentin staining of paraffinized tumor samples. Therefore, Vimentin positivity is not an accurate diagnostic feature of malignant RCCs due to the spliced Vim3 being detectable with the currently used antibodies against the N-terminal sequence.

abnormal growth of neoplastic cells) that appears enlarged in size. Tumor is not synonymous with cancer. While cancer is by definition malignant, a tumor can be benign, premalignant, or malignant, or can represent a lesion without any cancerous potential whatsoever. A malignant tumor contrasts with a non-cancerous benign tumor in that a malignancy is not self-limited in its growth, is capable of invading into adjacent tissues, and may be capable of spreading to distant tissues. A benign tumor has none of those properties. Renal tumors according to the present invention are tumors on or in the kidney. They may also be present in patients as an abdominal mass, hematuria, abdominal pain, or manifest themselves at first in a paraneoplastic syndrome that seems unrelated to the kidney.

The term "sample" in the context of the present invention may be any renal tumor sample, i.e. a sample including renal tumor cells. It may be tissue sample, a solid sample, a liquid sample, a cell sample, tissue section etc. Suitable methods for obtaining a sample are known in the art and include an excisional biopsy, an incisional biopsy, a core biopsy or a needle aspiration biopsy or other common methods used in the art.

The sample may be used in the diagnosis of benign oncocytoma. Diagnosis refers both to the process of attempting to determine or identify a possible disease or disorder (and diagnosis in this sense can also be termed diagnostic procedure), and to the opinion reached by this process (also being termed diagnostic opinion). From the point of view of statistics the diagnostic procedure may involve a classification test.

The feature "differentiate a benign oncocytoma from malignant renal cell carcinoma" in the context of the present invention is defined as being capable to distinguish a benign oncocytoma from a renal cell carcinoma. After having carried out the method to differentiate according to the present invention, the experimenter or physician or person skilled in the art will be able to define a renal tumor as benign oncocytoma or malignant renal cell carcinoma.

In order to do so, he will detect the presence or absence of Vim3 protein in the sample derived from a renal tumor. He may qualitatively and/or quantitatively determine the level or concentration or amount of Vim3 in the sample in question. Many methods for detecting or determining the presence or the level or concentration or amount of a protein in a sample are known in the art and may be used in the context of the present invention. Exemplary methods are described therein and include immuno-electrophoresis, immuno-blotting, Western blot, spectrophotometry, enzyme assay. For example the ELISA (Enyzme Linked Immunosorbent Assay) method may be applied to the present invention. For this, Vim3 is applied to a surface. Then, a further specific antibody is applied over the surface so it can bind to Vim3. This antibody is linked to an enzyme, and, in the final step, a substance containing the enzyme's substrate is added. The subsequent reaction produces a detectable signal, most commonly a color change in the substrate. The level of color change is related to the amount of Vim3 protein. However there are alternative methods of detection and quantification known in the art.

According to the present invention the presence of Vim3 in the sample is indicative of a benign oncocytoma and the absence is indicative of malignant renal cell carcinoma. Presence of Vim3 protein means that the level or concentration or amount of Vim3 in the sample in question is significantly different from that of a control or the background.

The person skilled in the art knows statistical procedures to assess whether two values are significantly different from each other such as Student's t-test or chi-square test. Furthermore, the skilled person knows how to select a suitable control. The control value or background value may be obtained by carrying out the method of the present invention additionally and simultaneously with a control, background or blank sample. Alternatively, it may be a value determined previously, e.g. a value provided by a third person, e.g. the manufacturer of laboratory equipment or a published value known from the art.

Preferably, the term "presence" reflects a situation in which the detected or determined value is at least 2-fold, 3-fold, 4-fold, 5-fold, 6-fold, 7-fold, 8-fold, 9-fold ort 10-fold more than the control or background value.

Preferably, the term "absence" reflects a situation in which the detected or determined value is at most 150%, 140%, 130%, 120% or 110% of the control or background value.

Hence, the present invention allows for a facilitated diagnosis of benign oncocytoma and the differentiation of a benign oncocytoma from malignant renal cell carcinoma using standard methods and gives accurate and robust results which substantially reduces the risk of misdiagnosis for the patient.

In a preferred embodiment of the present invention, the presence or absence of Vim3 protein is detected by detecting Vim3 protein expression in the sample. General protein detection methods in the art which are suitable for methods of diagnosis of benign oncocytoma or differentiation of benign oncocytoma from malignant renal cell carcinoma are immuno-electrophoresis, immuno-blotting, Western blot, spectrophotometry or enzyme assay for example but not limited to these.

More preferably, Vim3 protein expression may be detected using an agent specific for Vim3 protein, particularly an antibody or fragment or variant thereof, specific for Vim3 protein.

The term "agent" in relation to the present invention refers to any molecule, chemical entity or substance that is specific for Vim3, particularly the unique C-terminal end, such that it allows Vim3 to be distinguished, detected or separated in order for its level to be determined quantitatively or qualitatively in the diagnosis of benign oncocytoma or differentiating benign oncocytoma from renal cell carcinoma. The agent may be a protein, a small chemical compound, a ligand, especially an antibody or fragment or variant thereof.

In another preferred embodiment of the present invention, the presence or absence of Vim3 protein is detected by methods including labeled specific antibodies such as immunostaining, enzyme-linked immunosorbent assay (ELISA) or fluorescence in-situ hybridization.

In another preferred embodiment of the current invention, protein expression for Vim3 can similarly be detected using an agent specific for Vim3 mRNA, particularly one or more primer(s) specific for mRNA.

The quantification of mRNA from a renal tumor sample can be used to reflect the corresponding amount of protein in a sample. Reverse transcription polymerase chain reaction (RT-PCR) using primers may be used to determine this quantity. This technique is commonly used in molecular biology to detect RNA expression levels. RT-PCR is used to qualitatively detect gene expression through creation of complementary DNA (cDNA) transcripts from RNA. RT-PCR is used to quantitatively measure the amplification of DNA using fluorescent probes. RT-PCR is used to clone expressed genes by reverse transcribing the RNA of interest into its DNA complement through the use of reverse transcriptase. Subsequently, the newly synthesized cDNA is amplified using traditional PCR and quantified. However there are alternative methods of detection and quantification known in the art. Suitable primers for use as part of this invention are shown in table 2.

A primer according to the present invention is understood to be a strand of nucleic acid that serves for the synthesis of mRNA that is specific e.g. for the Vim3 protein. These primers can be made by known oligonucleotide synthetic methods such as the phosphoramidite synthetic method or other methods known in the art. Exemplary primers are given in table 2, e.g. the sequences of SEQ ID NO: 5 or 7 for Vim3 mRNA.

More preferably, the Vim3 mRNA may be detected by in-situ hybridization or PCR. In-situ hybridization is a type of hybridization that uses a labeled complementary DNA or RNA strand (i.e., probe) to localize a specific DNA or RNA sequence in a portion or section of tissue (in situ), or, if the tissue is small enough in the entire tissue, in cells and in circulating tumor cells (CTCs). Polymerase chain reaction (PCR) is used to amplify a single or a few copies of a piece of RNA or DNA across several orders of magnitude, generating thousands to millions of copies of a particular DNA or RNA sequence. Alternatively, Vim3 mRNA can be detected by any other known methods in the art. These methods include but are not limited to methods such as Northern blot analysis, nuclease protection assay (NPA) and reverse transcription-polymerase chain reaction.

In another preferred embodiment the method of the present invention further comprises the step of
a) detecting the presence or absence of the full length Vimentin protein in the sample, wherein the absence of full length Vimentin in the sample is indicative for a benign oncocytoma; and/or
b) determining the PKC level in the sample, wherein an increased PKC level relative top a control is indicative of benign oncocytoma In a preferred embodiment, the detection of the presence or absence of the full length Vimentin protein by using full length Vimentin protein-specific antibody (e.g. the one used for the examples) or full length Vimentin mRNA-specific primer(s) (e.g. the one used for the examples, see Table 2) and/or the determining of the PKC level is performed by using PKC-specific antibody or PKC-specific primer(s), which are well known in the art and available from commercial suppliers. Preferably, PKC is PKC α.

Alternatively, the method described above may be carried out by determining the level, amount or concentration of Vim3 and full length Vimentin, wherein a significantly increased level, amount or concentration of Vim3 and a significantly decreased level of full length Vimentin is indicative of oncocytoma. The increase or decrease is relative to a control, particularly to the level, amount or concentration of Vim3 and full length Vimentin in a renal carcinoma. The increase and decrease may be at least 2-fold, 3-fold, 4-fold, 5-fold, 6-fold, 7-fold, 8-fold, 9-fold ort 10-fold than the control.

The sample taken as part of the invention may be taken from a renal tumour, wherein the renal tumor is preferably from a mammal, such as a horse, a dog, a cat, a camel, or a cow, especially a human. Mammals may be defined as any various warm-blooded vertebrate animals of the class mammalia, including humans.

The method of diagnosis of a benign oncocytoma, or the method to differentiate a benign oncocytoma from a malignant renal cell carcinoma, can be conveniently carried out in practice using kits as part of the present invention.

Accordingly, a further aspect of the present invention relates to
i) an agent for detecting the presence or absence of Vim3 mRNA in a sample derived from a human renal tumor, particularly as defined above in the context of the present invention;
ii) optionally the antibody or primer(s) for the full length Vimentin and/or PKC as defined above in the context of the present invention; and
iii) instructions for carrying out the method.

Elements of these kits can be used in conjunction with current laboratory detection methods known in the art such as immuno-electrophoresis, immuno-blotting, Western blot, spectrophotometry, immune histology, ELISA in-situ hybridization or PCR, Northern blot analysis, nuclease protection assay (NPA) and reverse transcription-polymerase chain reaction (RT-PCR) to name but a few.

The agents employed in the kits may comprise antibodies and primers which are specific to allow detection of Vim3 mRNA, Vim3 protein, PKCα protein or PKC α mRNA, in particular the antibody specific for Vim3 protein e.g. the antibody specific for the unique C-terminal 8 amino acids of Vim3 (RGKHFISL: SEQ ID No: 2). In principle, any antibody or primer that binds specifically to Vim3 mRNA, Vim3 protein, but not full length Vimentin, is capable of being used in a method of diagnosis of a benign oncocytoma or the method to differentiate a benign oncocytoma from a malignant renal cell carcinoma. The term "agent" has been previously defined and included as part of the present invention.

Test kits according to the present invention include one or more reagents useful for practicing one or more methods according to the present disclosure. A kit generally includes a package with one or more containers holding the reagents, as one or more separate compositions or, optionally, as a mixture if reagents are compatible. The kit can also include other material(s), which may be desirable from a user standpoint, such as a buffer(s), a diluent(s), a standard(s), and/or any other material useful in sample processing, washing, or conducting any other step of the assay.

Kits according to the present disclosure can include a solid phase and a capture agent affixed to the solid phase, wherein the capture agent is an antibody specific for the analyte being assessed in the test sample. The solid phase may comprise a material such as a magnetic or paramagnetic particle including a microparticle, a bead, a test tube, a microtiter plate, a cuvette, a membrane, a scaffolding molecule, a quartz crystal, a film, a filter paper, a disc or a chip.

Test kits according to the invention preferably include instructions for carrying out one or more of the methods of the invention. Instructions included in kits of the invention can be affixed to packaging material or can be included as a package insert. While the instructions are typically written or printed materials they are not limited to such. Any medium capable of storing such instructions and communicating them to an end user is contemplated by this invention. Such media include, for example, computer media including, but are not limited to, electronic storage media (e.g., magnetic discs, tapes, cartridges, chips), optical media (e.g., CD ROM), and the like. As used herein, the term "instructions" can include the address of an internet site that provides the instructions.

In another aspect the present invention relates to an antibody or fragment or variant thereof specific for Vim3 protein. Preferably, the antibody or fragment or variant thereof is specific for the last 8 amino acids of the unique C-terminal of Vim3 protein only (RGKHFISL: SEQ ID No: 2), allowing these two structures to bind together with precision. In particular, the antibody will not bind to full length Vimentin which is key in diagnosing benign oncocytoma and differentiating benign oncocytoma from renal cell carcinoma.

A suitable antibody has been designed using the last 8 amino acids of the unique C-terminal ending of Vim3 as a target. The antibody binds specifically to Vim3 protein, but not the full length Vimentin, as shown in the Examples.

In terms of the present invention the antibody (Ab) is defined as an immunoglobulin (Ig) or glycoprotein, which is Y-shaped with two large heavy chains and two small light chains. However the antibody may also be an active fragment or active variant thereof that is specific to Vim3. The antibodies used as part of the invention are purified. Antibody purification can involve selective enrichment or specific isolation of antibodies from serum, ascites fluid or cell culture supernatant of a hybridoma cell line. Purification methods may range from very crude to highly specific.

"Full length" or "complete" antibodies refer to proteins that comprise two heavy (H) and two light (L) chains inter-connected by disulfide bonds. With regard to the term "complete antibody", any antibody is meant that has a typical overall domain structure of a naturally occurring antibody (i.e. comprising a heavy chain of three or four constant domains and a light chain of one constant domain as well as the respective variable domains), even though each domain may comprise further modifications, such as mutations, deletions, or insertions, which do not change the overall domain structure.

An "antibody fragment" also contains a part of a full length antibody and exhibits essentially the same function and specificity as the complete antibody of which the fragment is derived from. Examples thereof include Fab, F(ab')2, Fab', or scFv. Variable domains (Fvs) are the smallest fragments with an intact antigen-binding domain consisting of one VL and one VH. Such fragments, with only the binding domains, can be generated by enzymatic approaches or expression of the relevant gene fragments, e.g. in bacterial and eukaryotic cells. Different approaches can be used, e.g. either the Fv fragment alone or 'Fab'-fragments comprising one of the upper arms of the "Y" that includes the Fv plus the first constant domains. These fragments are usually stabilized by introducing a polypeptide link between the two chains which results in the production of a single chain Fv (scFv). Alternatively, disulfide-linked Fv (dsFv) fragments may be used. The binding domains of fragments can be combined with any constant domain in order to produce full length antibodies or can be fused with other proteins and polypeptides. A recombinant antibody fragment is the single-chain Fv (scFv) fragment. Dissociation of scFvs results in monomeric scFvs, which can be complexed into dimers (diabodies), trimers (triabodies) or larger aggregates such as TandAbs and Flexibodies. The antibody may be a Fab, a Fab', a F(ab')2, a Fv, a disulfide-linked Fv, a scFv, a (scFv)2, a bivalent antibody, a bispecific antibody, a multi-specific antibody, a diabody, a triabody, a tetrabody or a minibody.

In another preferred embodiment, the antibody according to the present invention may be a monoclonal antibody, a chimeric antibody or a humanized antibody. Monoclonal antibodies are monospecific antibodies that are identical because they are produced by one type of immune cell that are all clones of a single parent cell. A chimeric antibody is an antibody in which at least one region of an immunoglobulin of one species is fused to another region of an immunoglobulin of another species by genetic engineering in order to reduce its immunogenicity. For example murine $V_L$ and $V_H$ regions may be fused to the remaining part of a human immunoglobulin. A particular type of chimeric antibodies are humanized antibodies. Humanized antibodies are produced by merging the DNA that encodes the CDRs of a non-human antibody with human antibody-producing DNA. The resulting DNA construct can then be used to express and produce antibodies that are usually not as immunogenic as the non-human parenteral antibody or as a chimeric antibody, since merely the CDRs are non-human.

An "antibody variant" contains a part of a full length antibody and further amino acids and exhibits essentially the same function and specificity as the complete antibody of which the fragment is derived from. Particularly, it may be desirable, to add a marker for detection of the molecule to the same. Suitable markers include without limitation a tag (e.g. 6 His (or HexaHis) tag, STREP-TAG® marker, HA tag, c-myc tag or glutathione S-transferase (GST) tag), fluorescence marker (e.g. FITC, fluorescein, rhodamine, CY® fluorescent dyes or ALEXA FLUOR® fluorescent chemicals), enzyme label (e.g. penicillinase, horseradish peroxidase and alkaline phosphatase), a radiolabel (e.g. $^3H$, $^{32}P$, $^{35}S$, $^{125}I$ or $^{14}C$). Additionally, the antibody variant may be added to a support, particularly a solid support such as an array, bead (e.g. glass or magnetic), a fiber, a film etc. The skilled person will be able to adapt the antibody of the present invention and a further component to the intended use by choosing a suitable further component.

Another aspect of the present invention relates to a hybridoma cell line capable of producing an antibody, a fragment or a variant thereof for Vim3. The hybridoma cells are generated by well-known conventional techniques. In the context of the present invention the hybridoma cell is able to produce an antibody specifically binding to Vim3. The hybridoma cell can be generated by fusing a normal-activated, antibody-producing B cell with a myeloma cell. In particular, the hybridoma cell may be produced as follows: B-cells are removed from the spleen of an animal that has been challenged with the relevant antigen. These B-cells are then fused with myeloma tumor cells that can grow indefinitely in culture. This fusion is performed by making the cell membranes more permeable. The fused hybrid cells (called hybridomas), being cancer cells, will multiply rapidly and indefinitely and will produce large amounts of the desired antibodies. They have to be selected and subsequently cloned by limiting dilution. Supplemental media containing Interleukin-6 (such as briclone) are usually essential for this step. Selection occurs via culturing the newly fused primary hybridoma cells in selective-media, specifically media containing 1× concentration HAT for roughly 10-14 days. After using HAT it is often desirable to use HT containing media. Cloning occurs after identification of positive primary hybridoma cells.

In another further aspect, the use of Vim3 for the diagnosis of benign oncocytoma is included as part of the present invention. The terms "Vim3", "diagnosis" and "benign oncocytoma" have been previously defined already in the present invention in the context of this aspect of the invention and the above definitions, embodiments and methods are also applicable to this use.

In yet a further aspect, the use of Vim3 to differentiate a benign oncocytoma from malignant renal cell carcinoma is included as part of the present invention. The terms "Vim3", "differentiate", "benign oncocytoma", "malignant" and "renal cell carcinoma" have been previously defined already in the present invention in the context of this aspect of the invention and the above definitions, embodiments and methods are also applicable to this use.

The invention is not limited to the particular methodology, protocols, and reagents described herein because they may vary. Further, the terminology used herein is for the purpose of describing particular embodiments only and is not intended to limit the scope of the present invention. As used herein and in the appended claims, the singular forms "a", "an", and "the" include plural reference unless the context clearly dictates otherwise.

Similarly, the words "comprise", "contain" and "encompass" are to be interpreted inclusively rather than exclusively.

Unless defined otherwise, all technical and scientific terms and any acronyms used herein have the same meanings as commonly understood by one of ordinary skill in the art in the field of the invention. Although any methods and materials similar or equivalent to those described herein can be used in the practice of the present invention, the preferred methods, and materials are described herein.

The invention is further illustrated by the following example, although it will be understood that the examples are included merely for purposes of illustration and are not intended to limit the scope of the invention unless otherwise specifically indicated.

FIGURES

FIG. 1. Evaluation of Vim3 antibody. In FIG. 1A, immune histology showing expression of Vim3 in colonic crypt epithelium and in lymphocytes. In FIG. 1B, Western blot analysis after macrodissection of crypt epithelium and lymphocytes. β-actin as loading control.

Figure 2:
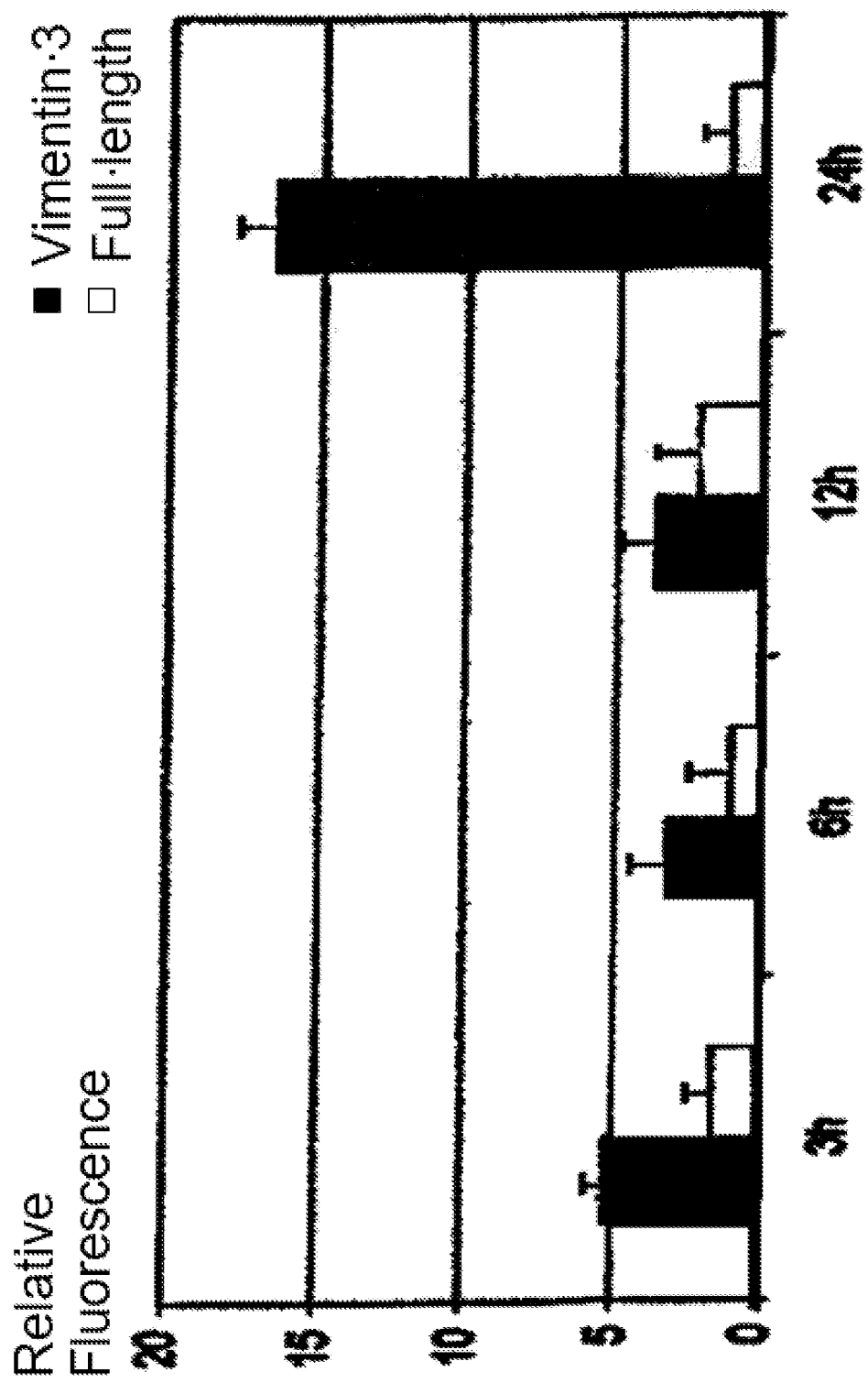

FIG. 2. Induction of Vim3 isoform after TGF-β treatment in Caki-1 cells. TGF-β induces Vim3 after 3 and 24 hrs, with little changes in the amount of the full length molecule. At 3 hrs, $p<0.5$; at 24 hrs. $p<0.001$; at 6 and 12 hrs no significance.

Figure 3:
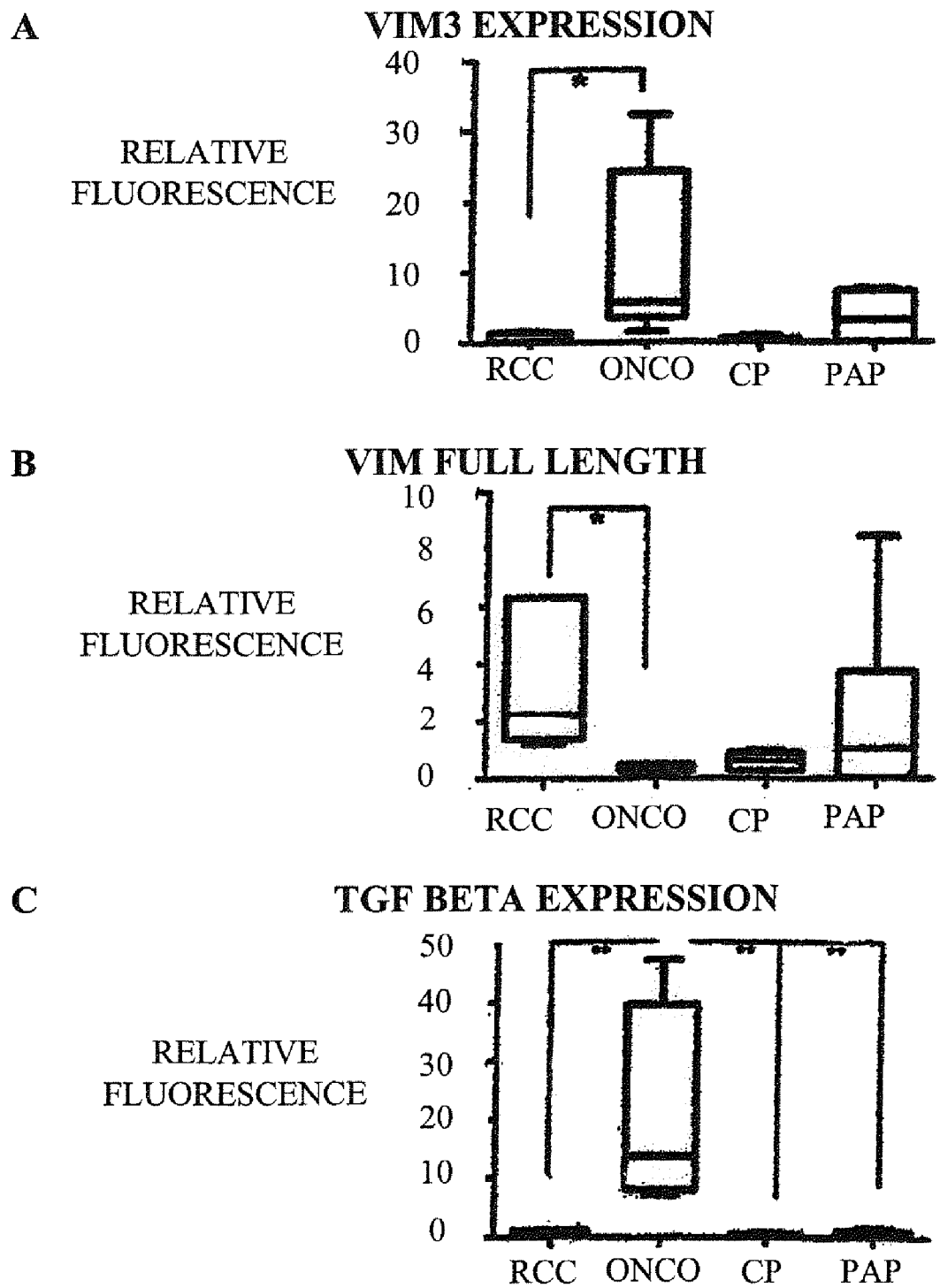

FIG. 3. FIG. 3A. qRT-PCR analysis for Vim3, FIG. 3B. full length Vimentin, and FIG. 3C. TGF-β in oncocytoma vs. clear cell renal cell carcinoma (RCC), chromphobe RCC (CP), and papillary RCC (Pap). Mean+/−SD; $p<0.5$ for Vim3 and vimentin for RCC vs. oncocytoma; $p<0.01$ for TGF-β between oncocytoma and all other RCCs. β-actin was used for neutralization.

Figure 4:
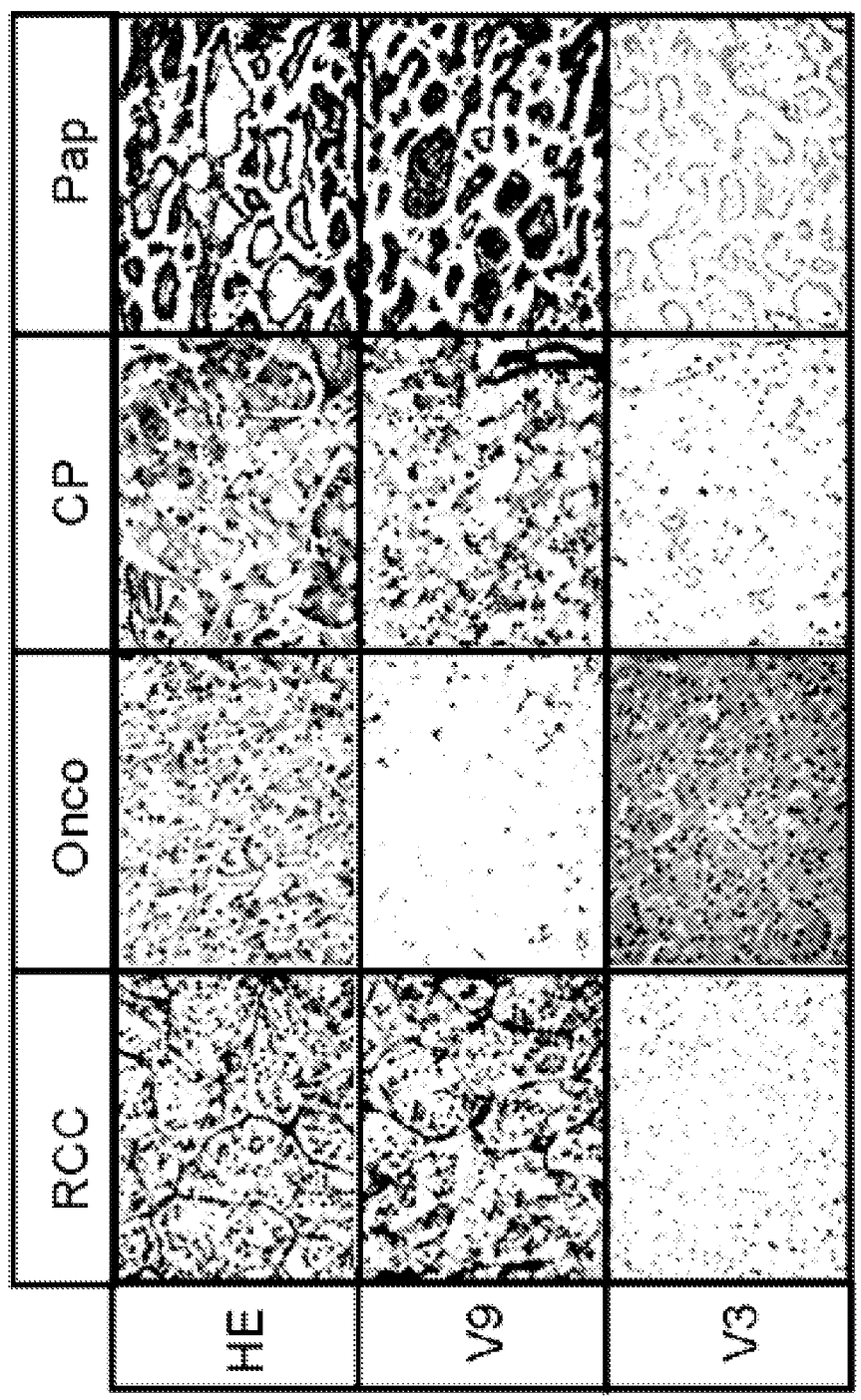

FIG. 4. Expression pattern between oncocytoma and RCCs. Full-length Vimentin positive tumor cells are observed in clear cell and papillary RCCs, while Vim3 positive cells are only found in oncocytoma, which is otherwise negative for full-length Vimentin. HE staining of typical tumor morphology; original magnification ×400.

FIG. 5. Immune fluorescence staining of paraffin embedded kidney samples.

FIG. 6 qRT-PCR results showing the Vim3 expression of the different kidney tumors. The Vim3 expression in Oncocytoma is significant (*$p<0.05$, **$p<0.01$).

REFERENCES

1. Hamperl: Über das Vorkommen von Oncocyten in verschiedenen Organen und ihren Geschwülsten, Arch Pathol Anat 1936, 298:327-375
2. Kataoka R, Hyo Y, Hoshiya T, Miyahara H, Matsunaga T: Ultrastructural study of mitochondria in oncocytes, Ultrastruct Pathol 1991, 15:231-239
3. Zippel: Zur Kenntnis der Onkocyten, Virchows Arch 1942, 308:360-362
4. Klein M J, Valensi Q J: Proximal tubular adenomas of kidney with so-called oncocytic features. A clinicopathologic study of 13 cases of a rarely reported neoplasm, Cancer 1976, 38:906-914
5. Oxley J D, Sullivan J, Mitchelmore A, Gillatt D A: Metastatic renal oncocytoma, J Clin Pathol 2007, 60:720-722
6. Osunkoya A O, Cohen C, Lawson D, Picken M M, Amin M B, Young A N: Claudin-7 and claudin-8: immunohistochemical markers for the differential diagnosis of chromophobe renal cell carcinoma and renal oncocytoma, Hum Pathol 2009, 40:206-210
7. Waldherr R, Schwechheimer K: Co-expression of cytokeratin and vimentin intermediate-sized filaments in renal cell carcinomas. Comparative study of the intermediate-sized filament distribution in renal cell carcinomas and normal human kidney, Virchows Arch A Pathol Anat Histopathol 1985, 408:15-27
8. Hes O, Michal M, Kuroda N, Martignoni G, Brunelli M, Lu Y, Adley B P, Alvarado-Cabrero I, Yang X J: Vimentin reactivity in renal oncocytoma: immunohistochemical study of 234 cases, Arch Pathol Lab Med 2007, 131:1782-1788
9. Ivaska J, Pallari H M, Nevo J, Eriksson J E: Novel functions of vimentin in cell adhesion, migration, and signaling, Exp Cell Res 2007, 313:2050-2062
10. Thakkar D, Shervington L, Shervington A: Proteomic studies coupled with RNAi methodologies can shed further light on the downstream effects of telomerase in glioma, Cancer Invest 2011, 29:113-122
11. Malakoutikhah M, Gomara M J, Gomez-Puerta J A, Sanmarti R, Haro I: The use of chimeric vimentin citrullinated peptides for the diagnosis of rheumatoid arthritis, J Med Chem 2011, 54:7486-7492
12. von Brandenstein M, Depping R, Schafer E, Dienes H P, Fries J W: Protein kinase C alpha regulates nuclear pri-microRNA 15a release as part of endothelin signaling, Biochim Biophys Acta 2011, 1813:1793-1802
13. Gerstung M, Roth T, Dienes H P, Licht C, Fries J W: Endothelin-1 induces NF-kappaB via two independent pathways in human renal tubular epithelial cells, Am J. Nephrol 2007, 27:294-300
14. von Brandenstein M G, Ngum Abety A, Depping R, Roth T, Koehler M, Dienes H P, Fries J W: A p38-p65 transcription complex induced by endothelin-1 mediates signal transduction in cancer cells, Biochim Biophys Acta 2008, 1783:1613-1622
15. von Brandenstein M, Pandarakalam J J, Kroon L, Loeser H, Herden J, Braun G, Wendland K, Dienes H P, Engelmann U, Fries J W: MicroRNA 15a, inversely correlated to PKC alpha, is a potential marker to differentiate between benign and malignant renal tumors in biopsy and urine samples, Am J Pathol 2012, 180:1787-1797
16. Sarria A J, Lieber J G, Nordeen S K, Evans R M: The presence or absence of a Vimentin-type intermediate filament network affects the shape of the nucleus in human SW-13 cells, J Cell Sci 1994, 107 (Pt 6):1593-1607
17. Georgatos S D, Blobel G: Lamin B constitutes an intermediate filament attachment site at the nuclear envelope, J Cell Biol 1987, 105:117-125
18. Spurny R, Gregor M, Castanon M J, Wiche G: Plectin deficiency affects precursor formation and dynamics of Vimentin networks, Exp Cell Res 2008, 314:3570-3580
19. Esue O, Carson A A, Tseng Y, Wirtz D: A direct interaction between actin and vimentin filaments mediated by the tail domain of Vimentin, J Biol Chem 2006, 281:30393-30399

EXAMPLES

Example 1

This example includes a method of preparing, diagnosing and differentiating benign oncocytomas. The details are described in the immune histology in the materials and methods section (1.3) and results are found in FIG. 4.

1. Materials and Methods 1.1 Antibody Design and Quantification

The Vim3 antibody was commercially designed (EZbiolabs), using the last 8 amino acids (RGKHFISL: SEQ ID No: 2) of the unique C-terminal ending of Vim3 as target. Its expression versus that of full length Vimentin V9 (sc-6260; Santa Cruz, Heidelberg) was analysed using immune histology on paraffin embedded colon mucosa biopsies from our pathology archive. Western Blot analysis of macro-dissected material of cryptal epithelial cells and lymphoid cells was performed for further evaluation and proof of specificity of the newly designed antibody.

1.2 Cell Culture

Caki-1 cells were cultured as previously described (von Brandenstein et al, 2011). For TGF-β (Sigma Aldrich, Schnelldorf, Germany) stimulation 5 ng/ml were used. Before cell treatments, cells were serum starved for 24 h.

1.3 Immune Histology

Paraffin-embedded tissue sections (4 μm thick) were deparaffinized by incubation for 2-5 minutes in xylene, followed by 2-3 minutes in 100% ethanol, and 1 minute in 95% ethanol; and then rinsed with distilled water. The slides were incubated with a specific serum blocker (anti-rabbit) for 30 minutes to avoid unspecific binding. After that incubation period, the slides were re-incubated for 1 hour at room temperature with specific primary antibodies (Vimentin 3, EZBiolab, Inc. Carmel, USA or Vimentin V9, sc-6260, Santa Cruz, Heidelberg, Germany). After washes with PBS-Tween 20 (Phosphate Buffered Saline), sections were incubated with a secondary anti-rabbit antibody (Santa Cruz, Heidelberg, Germany). After rinsing with PBS TWEEN® 20 surface active agent, slides were re-incubated for 2 minutes in 95% ethanol, followed by 2-3 minutes in 100% methanol, counterstained with H&E (Hematoxylin and Eosin), and cover-slipped.

1.4 Ethics

Since human materials were used, procedures were followed as outlined in accordance with ethical standards formulated in the Declaration of Helsinki 1975, with pre-approval by the Ethics Committee at the University Hospital, Koeln (reference no. 09-232).

TABLE 1

Tumor types and localisations

| patient number | Diagnose | Sex | Age | tumor size [cm] |
|---|---|---|---|---|
| 1 | Normal | | Control | |
| 2 | kidney | | | |
| 3 | control | | | |
| 4 | | | | |
| 6 | Oncocytoma | female | 79 | 1.5 |
| 7 | | male | 48 | 4 |
| 8 | | male | 71 | 2 |
| 9 | | male | 67 | 10 |
| 10 | | male | 73 | 6 |
| 11 | Chromoph | male | 63 | 3.3 |
| 12 | RCC | male | 62 | 5.5 |
| 13 | | female | 70 | 2.8 |
| 14 | | female | 55 | 4 |
| 15 | | male | 78 | 2.3 |
| 17 | Papillary | male | 74 | 1.5 |
| 18 | RCC | male | 54 | 1.5 |
| 19 | | male | 77 | 6 |
| 22 | | male | 49 | 1.5 |
| 23 | | male | 63 | 1.5 |
| 24 | Clear cell | female | 81 | 3.7 |
| 25 | RCC | female | 71 | 7 |
| 26 | | female | 42 | 7.8 |
| 27 | | female | 87 | 3.1 |
| 28 | | female | 61 | 6 |

1.5 Quantitative Real-Time PCR (qRT-PCR)

The qRT-PCR was performed as previously described (Gerstung et al., 2007 and vonBrandenstein et al., 2008). For quantitative analysis, β-actin was measured. All samples were normalized to β-actin as the reference gene. All experiments were performed in triplicate. Relative fluorescence was calculated using the ΔΔ-CT method, as outlined in user bulletin 2 (PE Applied Biosystems, Darmstadt, Germany). The statistical significance of qPCR values at different time points was assessed by the Student's paired t-test. Table 2 provides primer information.

TABLE 2

Primers used in this invention.

| Gene | Sequence | Annealing Temp. | cycles |
|---|---|---|---|
| β-Actin | Forw. 5'-TTGGCAATGAGCGGTTCCGCTG-3' (SEQ ID No: 3) Rev. 5'-TACACGTGTTTGCGGATGTCCAC-3' (SEQ ID No: 4) | 55° C. | 40x |
| Vimentin, full length | Forw. 5'-GAGAACTTTGCCGTTGAAGC-3' (SEQ ID No: 5) Rev. 5'-TCCAGCAGCTTCCTGTAGGTG-3' (SEQ ID No: 6) | 55° C. | 40x |
| Vim3 | Forw. 5'-GAGAACTTTGCCGTTGAAGC-3' (SEQ ID No: 5) Rev. 5'-GAAATAAAATGCTTACCCCTCAG-3' (SEQ ID No: 7) | 55° C. | 40x |
| TGF-β | Forw. 5'-GGGACTATCCACCTGCAAGA-3' (SEQ ID No: 8) Rev. 5'-CCTCCTTGGCGTAGTAGTCG-3' (SEQ ID No: 9) | 55° C. | 40x |

1.6 RNA-Extraction Paraffin Embedded Tissues and RT-PCR

Formalin-fixed and paraffinized (FFPE) human tissue samples from the archives of the Department of Pathology, University Hospital of Koeln, Koeln, Germany, were used. RNA extraction from FFPE tissue was performed according to the RNeasy FFPE kit (Qiagen, Germany). RNA quantification was accomplished using NanoDrop technology. The cDNA was obtained from 250 ng of RNA using random primers and SuperScript III reverse transcriptase, according to the manufacturer's protocol (Invitrogen, Darmstadt, Germany).

1.7 Western Blot

All Western blots were performed in triplicates as outlined in detail before (Gerstung et al., 2007). As loading control served β-actin (Santa Cruz, Heidelberg, Germany). Vimentin3 antibody was used in a 1:250 dilution, antibody (V9, Thermo Scientific) against full length Vimentin was employed in 1:1000 as recommended by the supplier.

Results

Vimentin splice isoform, called Vimentin3 (Vim3), is characterised as a potentially important structural cellular protein. Its unique structure leads to a 10 kDa smaller protein (FIG. 1B), which is more widely expressed than its full length counterpart, in particular in epithelial cells and in lymphocytes (FIG. 1A). However, it presents itself as typical mesenchymal derived structural molecule being upregulated by TGF-β stimulation. Interestingly, this can be demonstrated in renal tumor cells (Caki-1) (FIG. 2), which in addition demonstrated that the amount of upregulation for Vim3 exceed that for its full length counterpart. However, in normal renal proximal tubule cells vim3 can be identified without prior stimulation, while their tumor counterparts (Caki-1) are negative for vim3 when left untreated.

The importance of Vim3 for renal tubule cells was studied further. Vim3 was analysed versus full length Vimentin expression by qRT-PCR in renal tumors (FIG. 3). Surprisingly, while clear cell RCCs have high amounts of transcribed full length Vimentin, they are almost Vim3 negative. In contrast, the reverse is true for oncocytomas: while their negativity for full length vimentin is not surprising (and being a criteria for their identification), the levels for Vim3 are unexpectedly high. Since TGF-β could stimulate Vim3 (at least in Caki-1 cells) better than full length Vimentin, TGF-β levels were compared between those two tumor types. Correspondingly to the Vimentin type, high TGF-β levels associated with high Vim3 levels in oncocytomas were found and vice versa in RCCs. From the other two major RCC subtypes, the chromophobe RCC (CP) resembles its qRT-PCR (FIG. 3) and its immune histology (FIG. 4) results for Vimentin (being positive) and Vim3 (being negative) more closely that of a clear cell RCC, although some of its qRT-PCR positivity is probably caused by its vascular wall elements. The papillary RCC subtype (Pap) has some amount of Vimentin full length and Vim3 form detectable by qRT-PCR. However, the Vim3 signal is not strong enough to be appreciable by immune histology (FIG. 4), while a strong Vimentin (full length) staining can be easily detected. This result identifies Vim3 as potential immune histology marker for renal oncocytomas.

Currently, it is common practice in pathology, to differentiate renal cell carcinomas from carcinomas of histogenetically different origins by immune histology with cytokeratins and vimentin. In particular Vimentin positivity has been regarded as major hallmark not only for RCC in general but also to differentiate them from their benign counterparts, the oncocytomas. Since Vimentin positivity has been shown in oncocytomas, this diagnostic approach has been questionable, while the underlying mechanism has been elusive (Hes et al., 2007). From the present invention, it is claimed that by using an antibody against the unique C-terminal sequence of Vim3 "real" oncocytomas can be unequivocally identified. It was found that there is a reverse relationship between positivity for protein kinase C (PKC) α and miRNA 15a in renal tumors. In oncocytomas, high levels of PKC α are found, while miRNA 15a levels are low and the reverse is true in clear cell RCCs (von Brandenstein et al., 2012). Thus, an additional investigation was added regarding PKC α protein levels for those histogenetically questionable tumor cases. Interestingly, it was observed that full length Vimentin positive, oncocytic tumors show absent PKC α protein expression at least in the cell nucleus. This result indicates that these tumors have to be classified as eosinophilic variant of a clear cell RCC. Since their morphologic appearance on a H&E slide seems identical to a "true" oncocytoma, it is proposed that in case this differentiation has to be made, a immune histology for PKC α as well as an immune histology for Vim3 should be performed. The importance of such a potential explanation for routine pathologic diagnosis regarding the mystery of "Vimentin-positive oncocytomas" seemed to justify the current explanation though based on exemplary cases.

So far, an intracellular role of Vim3 has not been defined, while an intracellular role of the full length Vimentin molecule has been described in the literature as anchoring molecule for the nucleus (Sarria et al., 1994). Knowing the interaction of its full length counterpart, one may speculate about its intracellular importance. Since the N-terminal domain and the rod domain have not changed, binding partners such as ankyrin (Georgatos et al., 1987) and interactions with plectin (Spurny et al., 2008) should still be possible. In contrast, the missing tail and the unique amino acids of its C-terminal ending may result differences in the C-terminal interaction. Currently, the tail domain has been reported to be the binding and interactive site for F-actin (Esue et al., 2006) and lamin B (Georgatos et al., 1987). However, since in the case of Vim3 the major part of the C-terminus is still absent and the exact interaction sites for both molecules are presently unknown, further investigations have to be conducted in order to fully elucidate potential interaction or its absence between Vim3 and other structural binding partners.

Vim3 differentiates benign oncocytoma from malignant RCC variants by immune histology. In contrast, full length Vimentin positivity and negativity for Vim3 in an otherwise oncocytic tumors indicates that this tumor must be classified as variant of RCC and not as a benign oncocytoma.

Antibody Evaluation

Since Vimentin is commonly known primarily as mesenchymal marker, the Vim3 antibody was characterized using frozen sections of appendiceal tissue containing epithelial, mesenchymal and lymphatic tissue elements. FIG. 1 shows that Vim3 was expressed in colonic crypt epithelium, particularly in the regeneratively active part of the crypt, in mesenchymal cells, and in lymphocytes. A Western blot was performed to verify the expected size of the vim3 splice form being 47 kDa (FIG. 1), while the full length molecule was predictably 57 kDa.

Vim3 antibody binding pattern was also established in renal tissues. Vimentin full length molecule was demonstrable in different types of mesenchymal calls (such as fibroblasts, smooth muscle cells and others), and also in proximal tubule cells. In contrast, Vim3 could only be detected in proximal tubule cells.

TGF-β Stimulates Vim3 Expression

TGF-β is a known mediator of Vimentin expression. It was analysed to determine whether it could also stimulate Vim3 using Caki-1 cells, a known malignant cell line derived from proximal tubules. At different time points (3, 6, and 12 hrs) Vim3 was upregulated, being about twice the level of full length Vimentin. After 24 hrs Vim3 mRNA levels reached a peak being even 5 times higher (FIG. 2).

mRNA Detection of Vimentin, Vim3 and TGF-β

The full length molecule of Vimentin is used as a marker to differentiate benign oncocytomas, expected to be negative, from malignant renal cell carcinomas, particularly the clear cell subtype, being Vimentin positive. The qRT-PCR evaluation of renal tumors confirmed this finding in cases from our archive, while demonstrating that full length Vimentin was also minimally expressed in chromophobe RCCs. In contrast, papillary RCCs showed a moderate Vimentin full length expression (FIG. 3). The analysis of Vim3 mRNA revealed a reverse relationship between clear cell RCCs and oncocytomas compared to full length Vimentin: oncocytomas have high Vim3 mRNA levels and low levels of full length Vimentin mRNA. Chromophobe RCCs show low levels of vim3. Papillary RCCs have lower levels of Vim3 mRNA. This pattern is paralleled by detectable levels of TGF-β—mRNA being high in oncocytomas and very low in all other malignant RCC subtypes.

Protein Detection of Vim3 Versus Full Length Vimentin in Renal Tumors

By immune histology on paraffinized tissue slices from renal tumors, full length Vimentin protein was found strongly expressed in clear cell RCCs, and papillary RCCs. Chromophobe RCCs showed a weak reactivity with the antibody, while oncocytomas were negative. In contrast, Vim3 expression was strong in oncocytomas with all three malignant RCCs subtypes were negative.

Full Length Vimentin Positive, Vim3 Negative Oncocytic Tumors are Subtypes of Clear Cell RCCs Full length Vimentin positive oncocytic tumors were also found in accordance with cases reported in the literature. These cases were negative for Vim3, raising the question of their potential histogeneity from malignant RCCs. To substantiate this suspicion, additional qRT-PCR analysis was used for protein kinase C alpha (PKC α) and miRNA 15a. These tumors had high levels of miRNA 15a, while PKC α levels were very low.

Example 2

This example describes how Vimentin 3 (Vim3) differentiates between benign and malignant kidney tumors. Results can be found in FIGS. 5 and 6.

The Vim3 mRNA content of additional cases of Oncocytoma (10), chromophobe renal cell carcinomas (RCCs) (5), RCCs of the eosinophilic variant (5) as well as papillary RCCs (5) were analysed via quantitative real time PCR (qRT-PCR). Also different renal tumors were chosen randomly and immune fluorescence labelling of the paraffin embedded tissues were performed.

2. Materials and Methods

2.1 Quantitative Real-Time PCR (qRT-PCR)

The RNA was isolated with the RNeasy FFPE kit (Qiagen) according to the manufactures protocol.

The cDNA was obtained from 250 ng RNA using random primers and SuperScript® III reverse transcriptase according to the manufacturer's protocol (Invitrogen™). The RT-PCR was performed as previously described.

Either 1 μl of the previously isolated cDNA was used for real-time PCR analysis.

For quantitative analysis, β-actin was measured using the QuantiTect SYBR® Green PCR kit (Qiagen). All samples were normalized to β-actin as reference gene. All experiments were done in triplicate. Relative fluorescence was calculated using the $\Delta\Delta C_T$ method as outlined in user bulletin 2 (PE Applied Biosystems). The statistical significance of qRT-PCR values at different time points was assessed by Student's paired t test.

2.2 Immune Fluorescence of Paraffin Embedded Tissues

4 μm thick paraffin embedded tissue sections were deparaffinized by incubation for 1×10 min in Xylene, followed by 1×5 min 100% ethanol, and 1 min 70% ethanol then rinsed with distilled water. After that incubation period, the slides were re-incubated for 1 hour at room temperature with specific primary antibodies (Vim3) in 3% PBS milk. After washes with PBS, sections were incubated with a secondary FITC-anti-rabbit antibody (Santa Cruz). After rinsing with PBS, slides were counterstained with DAPI mounting medium (nuclear staining) and cover slipped.

Results

After immune fluorescence staining with the antibody either staining for Vim3 or Vimentin full length (C20-Santa Cruz), we detected only in the Oncocytoma cases a distinct Vim3 FITC signal. However, using the antibody against the full length Vimentin the exact opposite was observed: only the malignant RCC cases were stained.

qRT-PCR investigation of paraffin tissue yielded the identical result as obtained by the immune fluorescence. Regarding the shown results on protein level (FIG. 5), the obtained mRNA expression of Vim3 in the RCC variants is negligible (FIG. 6). However, the obtained expression of Vim3 in Oncocytoma is significant (*$p<0.05$, **$p<0.01$). FIG. 6 gives qRT-PCR results showing the Vim3 expression of the different kidney tumors.

The invention claimed is:

1. A method to differentiate a benign renal oncocytoma from malignant renal cell carcinoma, comprising the following steps:
   (i) providing a sample derived from a human renal tumor; and
   (ii) detecting the level of Vim3 protein in the sample
   (iii) comparing the level of Vim3 protein in the sample to the level of Vim3 protein in a control sample derived from malignant renal cell carcinoma;
   (iv) identifying the renal tumor as
      (a) a benign renal oncocytoma if the Vim3 protein level in the sample is at least 2-fold higher than the Vim3 protein level in the control sample, or as
      (b) a malignant renal cell carcinoma, if the Vim3 protein level in the sample is, at most, 150% of the level of Vim3 protein in the control sample; and
   (v) treating the human renal tumor with enucleation, if the human renal tumor is identified as a benign renal oncocytoma, or treating the human renal tumor with radical or partial nephrectomy if the human renal tumor is identified as a malignant renal cell carcinoma.

2. The method of claim 1, wherein the levels of Vim3 protein in the sample derived from a human renal tumor and the control sample are detected by using immunostaining or enzyme-linked immuno-sorbent assay (ELISA).

3. A method of treating a human who has a renal tumor, comprising:
   i) detecting the level of Vim3 protein in a sample from the renal tumor;
   ii) comparing the level of the Vim3 protein in the sample from the renal tumor to the level of Vim3 protein in a control sample derived from a malignant renal cell carcinoma; and
   iii) treating the human with radical or partial nephrectomy, if the Vim3 protein level detected in the sample from the renal tumor is, at most, 150% of the Vim3 protein level detected in the control sample derived from a malignant renal cell carcinoma, thereby indicating that the human's renal tumor is a malignant renal cell carcinoma; or treating the human with tumor enucleation, if the Vim3 protein level detected in the sample from the renal tumor is, at least, 2-fold higher than the Vim3 protein level detected in the control sample derived from a malignant renal cell carcinoma, thereby indicating that the human's renal tumor is a benign renal oncocytoma.

* * * * *

SEQUENCE LISTING

<160> NUMBER OF SEQ ID NOS: 9

<210> SEQ ID NO 1
<211> LENGTH: 431
<212> TYPE: PRT
<213> ORGANISM: Homo sapiens

<400> SEQUENCE: 1

```
Met Ser Thr Arg Ser Val Ser Ser Ser Tyr Arg Arg Met Phe Gly
1               5                   10                  15

Gly Pro Gly Thr Ala Ser Arg Pro Ser Ser Ser Arg Ser Tyr Val Thr
            20                  25                  30

Thr Ser Thr Arg Thr Tyr Ser Leu Gly Ser Ala Leu Arg Pro Ser Thr
            35                  40                  45

Ser Arg Ser Leu Tyr Ala Ser Ser Pro Gly Gly Val Tyr Ala Thr Arg
50                  55                  60

Ser Ser Ala Val Arg Leu Arg Ser Ser Val Pro Gly Val Arg Leu Leu
65                  70                  75                  80

Gln Asp Ser Val Asp Phe Ser Leu Ala Asp Ala Ile Asn Thr Glu Phe
                85                  90                  95

Lys Asn Thr Arg Thr Asn Glu Lys Val Glu Leu Gln Glu Leu Asn Asp
                100                 105                 110

Arg Phe Ala Asn Tyr Ile Asp Lys Val Arg Phe Leu Glu Gln Gln Asn
                115                 120                 125

Lys Ile Leu Leu Ala Glu Leu Glu Gln Leu Lys Gly Gln Gly Lys Ser
            130                 135                 140

Arg Leu Gly Asp Leu Tyr Glu Glu Glu Met Arg Glu Leu Arg Arg Gln
145                 150                 155                 160

Val Asp Gln Leu Thr Asn Asp Lys Ala Arg Val Glu Val Glu Arg Asp
                165                 170                 175

Asn Leu Ala Glu Asp Ile Met Arg Leu Arg Glu Lys Leu Gln Glu Glu
                180                 185                 190

Met Leu Gln Arg Glu Glu Ala Glu Asn Thr Leu Gln Ser Phe Arg Gln
            195                 200                 205

Asp Val Asp Asn Ala Ser Leu Ala Arg Leu Asp Leu Glu Arg Lys Val
210                 215                 220

Glu Ser Leu Gln Glu Glu Ile Ala Phe Leu Lys Lys Leu His Glu Glu
225                 230                 235                 240

Glu Ile Gln Glu Leu Gln Ala Gln Ile Gln Glu Gln His Val Gln Ile
                245                 250                 255

Asp Val Asp Val Ser Lys Pro Asp Leu Thr Ala Ala Leu Arg Asp Val
                260                 265                 270

Arg Gln Gln Tyr Glu Ser Val Ala Ala Lys Asn Leu Gln Glu Ala Glu
            275                 280                 285

Glu Trp Tyr Lys Ser Lys Phe Ala Asp Leu Ser Glu Ala Ala Asn Arg
290                 295                 300

Asn Asn Asp Ala Leu Arg Gln Ala Lys Gln Glu Ser Thr Glu Tyr Arg
305                 310                 315                 320

Arg Gln Val Gln Ser Leu Thr Cys Glu Val Asp Ala Leu Lys Gly Thr
                325                 330                 335

Asn Glu Ser Leu Glu Arg Gln Met Arg Glu Met Glu Glu Asn Phe Ala
                340                 345                 350

Val Glu Ala Ala Asn Tyr Gln Asp Thr Ile Gly Arg Leu Gln Asp Glu
            355                 360                 365
```

-continued

```
Ile Gln Asn Met Lys Glu Glu Met Ala Arg His Leu Arg Glu Tyr Gln
    370                 375                 380

Asp Leu Leu Asn Val Lys Met Ala Leu Asp Ile Glu Ile Ala Thr Tyr
385                 390                 395                 400

Arg Lys Leu Leu Glu Gly Glu Glu Ser Arg Ile Ser Leu Pro Leu Pro
                405                 410                 415

Asn Phe Ser Ser Leu Asn Leu Arg Gly Lys His Phe Ile Ser Leu
                420                 425                 430
```

<210> SEQ ID NO 2
<211> LENGTH: 8
<212> TYPE: PRT
<213> ORGANISM: Homo sapiens

<400> SEQUENCE: 2

```
Arg Gly Lys His Phe Ile Ser Leu
1               5
```

<210> SEQ ID NO 3
<211> LENGTH: 22
<212> TYPE: DNA
<213> ORGANISM: Artificial Sequence
<220> FEATURE:
<223> OTHER INFORMATION: Primer

<400> SEQUENCE: 3
ttggcaatga gcggttccgc tg                                           22

<210> SEQ ID NO 4
<211> LENGTH: 23
<212> TYPE: DNA
<213> ORGANISM: Artificial Sequence
<220> FEATURE:
<223> OTHER INFORMATION: Primer

<400> SEQUENCE: 4
tacacgtgtt tgcggatgtc cac                                          23

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
gagaactttg ccgttgaagc                                              20

<210> SEQ ID NO 6
<211> LENGTH: 21
<212> TYPE: DNA
<213> ORGANISM: Artificial Sequence
<220> FEATURE:
<223> OTHER INFORMATION: Primer

<400> SEQUENCE: 6
tccagcagct tcctgtaggt g                                            21

<210> SEQ ID NO 7
<211> LENGTH: 23
<212> TYPE: DNA
<213> ORGANISM: Artificial Sequence
<220> FEATURE:
<223> OTHER INFORMATION: Primer

```
<400> SEQUENCE: 7
gaaataaaat gcttacccct cag                                          23

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
gggactatcc acctgcaaga                                              20

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
cctccttggc gtagtagtcg                                              20
```